(12) United States Patent
Lavielle et al.

(10) Patent No.: US 7,053,108 B2
(45) Date of Patent: May 30, 2006

(54) INDOLINE COMPOUNDS

(75) Inventors: Gilbert Lavielle, La Celle Saint Cloud (FR); Olivier Muller, Pontoise (FR); Mark Millan, Le Pecq (FR); Alain Gobert, Rueil-Malmaison (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 40 days.

(21) Appl. No.: 10/813,347

(22) Filed: Mar. 30, 2004

(65) Prior Publication Data

US 2004/0192736 A1    Sep. 30, 2004

Related U.S. Application Data

(62) Division of application No. 10/400,358, filed on Mar. 27, 2003, now Pat. No. 6,759,421.

(30) Foreign Application Priority Data

Mar. 27, 2002 (FR) .................................. 02 03788

(51) Int. Cl.
*A61K 31/443* (2006.01)
*C07D 401/12* (2006.01)

(52) U.S. Cl. .................................. 514/339; 546/276.7
(58) Field of Classification Search ................ 514/339; 546/276.7
See application file for complete search history.

(56) References Cited

U.S. PATENT DOCUMENTS 6,221,884 B1 *  4/2001  Flaugh ........................ 514/339

OTHER PUBLICATIONS

Wijngaarden et al. Recl. Trav. Chim. Pays-Bas, 1993, 112:126-130.*
Barnes et al. Neuropharmacology, 1999, 38: 1083-1085 and 1107-1110.*
Berendsen, et al., *Psychopharmacology*, 1990, 101, 57-61.
Millan, et al., *European Journal of Pharmacology*, 1997, 325, 9-12.
O'Neill, et al., *Pharmacology, Biochemistry, and Behavior*, 1999, 63, 237-243.
Reavill, et al., *British Journal of Psychopharmacology*, 1999, 126, 572-574.
Herrick-Davis, et al., *Journal of Pharmacology and Experimental Therapeutics*, 2000, 295, 226-232.
Wood, et al., *Drug Development Research*, 2001, 54, 88-94.
Paiva, et al., *Psychopharmacology*, 1988, 96, 395-399.
Dugovic, *Journal Sleep Research*, 1992, 1, 1163-1168.
Landolt, et al., *Neuropsychopharmacology*, 1999, 21, 455-466.
Sharpley, et al., *Biological Psychiatry*, 2000, 47, 468-470.
Watson, et al., *Pharmacology, Biochemistry, and Behavior*, 1991, 39, 605-612.
Foreman, et al., *Life Sciences*, 1989, 45, 1263-1270.
Klint, et al., *Psychopharmacology*, 1995, 119, 291-294.
Hirschfeld, *Journal of Clinical Psychiatry*, 60 Suppl. 17:32-35, 1999.
Popova, et al., *Neuroendocrinology*, 2002, 76, 28-34.
Amesergide, LY-237733; *Pharmaproject*, Phase II Clinical Trial, 2005.
Koskinen, et al., *Pharmacology, Biochemistry and Behavior*, 2000, 66, 729-738.
White, et al., *Pharmacology, Biochemistry and Behaviour*, 1991, 39, 729-736.
Millan, et al., *Journal of Pharmacology and Experimental Therapeutics*, 2001, 298, 581-591.
Mundo, et al., *International Clinical Psychopharmacology*, 2000, 15, 69-76.

(Continued)

Primary Examiner—Patricia L. Morris
(74) Attorney, Agent, or Firm—Hueschen and Sage

(57) ABSTRACT

A compound of formula (I):

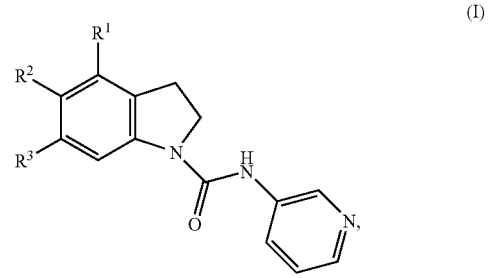

wherein:

$R^1$ and $R^2$ together form a benzo ring optionally substituted by halogen or by alkyl, alkoxy, cyano, nitro, hydroxy, amino, alkylamino, dialkylamino or trifluoromethyl, and $R^3$ represents hydrogen, or $R^1$ represents hydrogen, and $R^2$ and $R^3$ together form a benzo ring optionally substituted by halogen or by alkyl, alkoxy, cyano, nitro, hydroxy, amino, alkylamino, dialkylamino or trifluoromethyl, its enantiomers, diastereoisomers, and addition salts thereof with a pharmaceutically acceptable acid or base, and medicaments.

7 Claims, No Drawings

OTHER PUBLICATIONS

Millan, et al., *Prog. Neurobiol.*, 1999, 57, 1-164.
Millan, et al., *Prog. Neurobiol.*, 2002, 66, 355-474.
Kalkman, et al., *Int. J. Clin. Pharmacol. Res.*, 1997, 17, 75-77.
Kalkman, et al., *Naunyn Schmiedebergs. Arch. Pharmacol.*, 1994, 350, 225-229.
Kalkman, et al., *Life Sci.*, 1994, 54, 641-644.
Ro-60-0759, *Pharmaproject*, Preclinical Trial, 2005.
SB-243213, *Pharmaproject*, Phase I Clinical Trial, 2005.
LY-053857, *Pharmaproject*, Phase II Clinical Trial (2005).
Kant, *Pharmacol. Biochem. Behav.*, 1998, 59, 729-735.
Meneses, et al., *Behav. Brain Res.*, 1997, 87, 105-110.
Kant, *Pharmacol. Biochem. Behav.*, 1996, 53, 385-390.
Di Giovanni, et al., *Indian J. Exp. Biol.*, 2002, 40, 1344-1352.
De Deurwaerdere, et al., *Trends Pharmacol. Sci.*, 2001, 22, 502-504.
Millan, et al., *Neuropharmacology*, 1998, 37, 953-955.
Fox, et al., *Drug News and Perspectives*, 1999, 12:477-483.
Fox, et al., *Movement Disorders*, 2000, 15:1064-1069.
SM-3163, *Pharmaproject*, Phase II Clinical Trial (2005).

* cited by examiner

INDOLINE COMPOUNDS

This application is a divisional application of U.S. application Ser. No. 10/400,358, filed March 27, 2003, now U.S. Pat. No. 6,759,421.

FIELD OF THE INVENTION

The present invention relates to new indoline compounds having 5-HT$_{2C}$ antagonist properties, to a process for their preparation and to pharmaceutical compositions containing them.

BACKGROUND OF THE INVENTION

5-HT$_{2C}$ receptors exert inhibitory control over dopaminergic and noradrenergic transmission (Neuropharmacology, 1997, 36, 609, J. Psychopharmacol. 2000, 14 (2), 114–138). 5-HT$_{2C}$ antagonists are accordingly considered to be useful in the treatment of numerous pathologies of the central nervous system (CNS). There may be mentioned, without this list being entirely exhaustive, disorders such as anxiety (Br. J. Pharmacol., 1996, 117, 427), depression (Pharmacol. Biochem. Behav., 1988, 29, 819–820), impulsive disorders (Biol. Psych., 1993, 33, 3–14), sexual dysfunctions (J. Pharmacol., 1997, 11, 72), Parkinson's disease (Drug News Perspect., 1999, 12, 477), migraine (Life Sci., 1994, 54, 641–644), cognitive disorders (Neurosci. Biobehav. Rev., 1999, 23, 1111–1125), sleep disorders (Neuropharmacology, 1994, 33, (¾), 467–471), schizophrenia (Neurosci. Lett., 1996, 181, 65) and appetite disorders such as bulimia and anorexia (British J. Pharmacol., 1998, 123, 1707–1715).

The present invention relates to new indoline compounds which differ from the compounds of the Applications WO 9529177 and WO 9748699 not only in the absence of a pyridyloxy substituent on the 3-pyridylaminocarbonyl group of the indoline but also, especially, in the presence of a benzo group fused to the indoline group.

Surprisingly, those structural changes provide the compounds of the invention with pharmacological activities that are clearly superior to those of the compounds of the Applications WO 9529177 and WO 9748699. The compounds of the invention have been found, especially, to be very active by the oral route.

Use of the benzoindoline radical in the compounds of the invention has accordingly made possible a remarkable improvement in the pharmacological properties.

DETAILED DESCRIPTION OF THE INVENTION

More specifically, the present invention relates to compounds of formula (I):

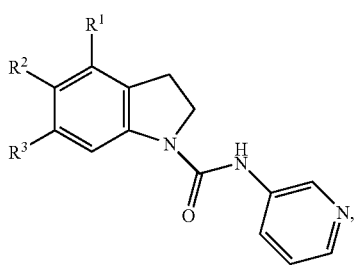

wherein:
R$^1$ and R$^2$ together form a benzo ring optionally substituted by a halogen atom or by an alkyl, alkoxy, cyano, nitro, hydroxy, amino, alkylamino, dialkylamino or trifluoromethyl group, and R$^3$ represents a hydrogen atom,
or
R$^1$ represents a hydrogen atom, and R$^2$ and R$^3$ together form a benzo ring optionally substituted by a halogen atom or by an alkyl, alkoxy, cyano, nitro, hydroxy, amino, alkylamino, dialkylamino or trifluoromethyl group, to their enantiomers and diastereoisomers, and to addition salts thereof with a pharmaceutically acceptable acid or base, it being understood that:
the term "alkyl" denotes a linear or branched hydrocarbon chain containing from 1 to 6 carbon atoms,
the term "alkoxy" denotes a linear or branched alkyl-oxy group containing from 1 to 6 carbon atoms.

Among the pharmaceutically acceptable acids there may be mentioned hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned sodium hydroxide, potassium hydroxide, triethylamine, tert-butylamine etc.

Preferred compounds of the invention are those wherein R$^1$ and R$^2$ together form a benzo ring which is unsubstituted or substituted by a group selected from methoxy and cyano, and R$^3$ represents a hydrogen atom.

Among the preferred compounds of the invention there may be mentioned, more especially, N-(3-pyridyl)-1,2-dihydro-3H-benzo[e]indole-3-carboxamide, 7-methoxy-N-(3-pyridyl)-1,2-dihydro-3H-benzo[e]indole-3-carboxamide, 6-cyano-N-(3-pyridyl)-1,2-dihydro-3H-benzo[e]indole-3-carboxamide and N-(3-pyridyl)-2,3-dihydro-1H-benzo[f]-indole-1-carboxamide.

The present invention relates also to a process for the preparation of compounds of formula (I), which process is characterised in that there is used as starting material a benzoindole of formula (II):

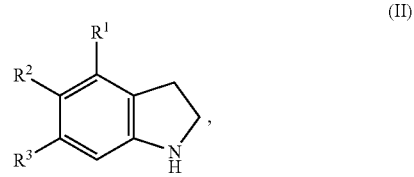

wherein R$^1$, R$^2$ and R$^3$ are as defined for formula (I),
which is condensed, under the action of heat, with a compound of formula (III):

wherein Y represents a group —N═C═O or —C(O)—N$_3$, to yield the compound of formula (I),
which may be purified, if necessary, according to a conventional purification technique,
which is separated, if desired, into its isomers (diastereoisomers and enantiomers) by a conventional separation technique,
which is converted, if desired, into addition salts thereof with a pharmaceutically acceptable acid or base, it being understood that the indoline of formula (II) is prepared according to known procedures, for example starting from the corresponding nitronaphthylacetonitrile compound.

The present invention relates also to pharmaceutical compositions comprising as active ingredient at least one compound of formula (I), alone or in combination with one or more inert, non-toxic, pharmaceutically acceptable excipients or carriers.

Among the pharmaceutical compositions according to the invention there may be mentioned more especially those that are suitable for oral, parenteral, nasal or transdermal administration, tablets or dragees, sublingual tablets, gelatin capsules, lozenges, suppositories, creams, ointments, dermal gels etc. . .

The useful dosage varies according to the age and weight of the patient, the nature and severity of the disorder, and also the administration route, which may be oral, nasal, rectal or parenteral. The unit dose generally ranges from 0.05 to 500 mg per 24 hours for treatment in 1 to 3 administrations.

The examples that follows illustrate, but do not limit, the invention.

The structures of the compounds described have been determined by conventional spectroscopic and spectrometric techniques.

The starting materials used are known products or are prepared according to known procedures.

Preparation 1

Step A: (2-Nitro-1-naphthyl)acetonitrile

Prepare a solution of 53.5 g (0.477 mol) of potassium tert.-butanolate in 400 ml of dimethylformamide. Cool the resulting solution to −10° C. and add thereto, over the course of about 1 hour, a solution of 40 g of 4-chlorophenoxyacetonitrile (0.24 mol) and 37 g of 2-nitronaphthalene (0.213 mol) in 200 ml of dimethylformamide. After 2 hours at −5° C., pour the mixture into 4 liters of water containing 1 liter of concentrated hydrochloric acid and extract the aqueous phase with 3×500 ml of dichloromethane. Wash the organic phase with 300 ml of water, dry it over magnesium sulphate, filter and then evaporate off the solvent.

65 g of product are obtained.

Recrystallise that 65 g from a mixture of cyclohexane/ethyl acetate: 50/50.

Step B: 3H-Benzo[e]indole

At ambient temperature and under 4 bars of hydrogen, hydrogenate 33 g of (2-nitro-1-naphthyl)acetonitrile (0.155 mol) dissolved in 630 ml of ethanol containing 10% water and 6.3 ml of pure acetic acid, using 19 g of 10% palladium-on-carbon. After absorption has ceased, filter off the catalyst, concentrate the solvent in vacuo and then take up the residue in 250 ml of dichloromethane; wash the organic phase with 100 ml of 0.1N potassium hydroxide solution and then dry the organic phase over magnesium sulphate, filter and concentrate.

The residue is purified by chromatography over silica, the eluant being cyclohexane/ethyl acetate: 80/20.

Step C: 2,3-Dihydro-1H-benzo[e]indole 10 g (0.06 mol) of the compound prepared in the previous step are dissolved in 50 ml of tetrahydrofuran. To the resulting solution, at 0° C., add 120 ml of borane/THF complex as a 1M solution in tetrahydrofuran, and then 120 ml of trifluoroacetic acid. After 30 minutes, add, at 0° C., 6 ml of water, stir for 15 minutes and then concentrate the mixture to dryness. The residue is taken up in 200 ml of dichloromethane and washed with 200 ml of 1N sodium hydroxide solution. The organic phase is dried over magnesium sulphate, filtered and concentrated.

Preparation 2

2,3-Dihydro-1H-benzo[e]indole

The experiment protocol for reducing 1H-benzo[f]indole is the same as that of Preparation 1, Step C. Synthesis of the starting material 1H-benzo[f]indole has been described in the literature [*Tetrahedron*, 49, 33, 7353 (1993); *Heterocycles*, 24, 7, 1845, (1986)].

Preparation 3

2,3-Dihydro-1H-benzo[e]indole-6-carbonitrile

Step A: N-(5-Cyano-2-naphthyl)acetamide

To 25 g of N-(5,6,7,8-tetrahydronaphth-2-yl)acetamide cooled to 0° C. add, successively, 70 ml of pure trimethylsilyl cyanide and then 30 g of dichlorodicyanoquinone in 70 ml of dichloromethane. After 3 hours at ambient temperature, again add a solution of 60 g of dichlorodicyanoquinone in 140 ml of dichloromethane. Stir at 20° C. for 12 hours and then heat at 60° C. for 8 hours.

After neutralising with saturated sodium hydrogen carbonate solution, the organic phase is separated off and washed with water. The residue obtained after concentration is purified by chromatography over silica gel using a mixture of cyclohexane/ethyl acetate: 80/20 as eluant.

Step B: N-(1-Bromo-5-cyano-2-naphthyl)acetamide

To a solution, cooled to −5° C., of 50 g (0.238 mol) of the product synthesised in the previous step in 500 ml of dichloromethane and 25 ml of pyridine, add 39.8 g of bromine dissolved in 200 ml of dichloromethane. Then stir vigorously for 4 hours at ambient temperature; subsequently dilute with 500 ml of dichloromethane, wash the organic phase twice with 300 ml of water, dry and concentrate. The residue is recrystallised from a mixture of dichloromethane/methanol: 50/50.

Step C: 6-Amino-5-bromo-1-naphthonitrile

Heat at 80° C., for 6 hours, a mixture of 12.5 g (0.043 mol) of the product synthesised in the previous step, 3.6 g of sodium hydroxide, 195 ml of methanol and 65 ml of water. After evaporating off the methanol, the aqueous phase is extracted twice with dichloromethane. The latter is subsequently dried and evaporated off. The residue is crystallised from a dichloromethane/methanol mixture.

Step D: Ethyl 1-bromo-5-cyano-2-naphthylcarbamate

Add, at 0° C., 19 ml of ethyl chloroformate to a solution of 33 g (0.133 mol) of the product synthesised in the previous step in 200 ml of pyridine. After 1 hour at 5° C., evaporate off the solvent, take up the residue in 500 ml of dichloromethane, wash the organic phase 3 times with 100 ml of 0.1N hydrochloric acid and then with 200 ml of 10% sodium hydrogen carbonate solution and finally once with water. The residue obtained by evaporation is recrystallised from a dichloromethane/methanol mixture.

Step E: Ethyl 5-cyano-1-[(trimethylsilyl)ethynyl]-2-naphthylcarbamate

In a steel reactor, mix 14.1 g (0.044 mol) of the product synthesised in the previous step, 11 ml of trimethylsilylacetylene, 13 ml of triethylamine, 670 mg of cuprous iodide and 1.54 g of dichloro-bis(triphenylphosphine)palladium. Then close the reactor and heat the reaction mixture at 80° C. for 4 hours. Dilute with 200 ml of dichloromethane and 100 ml of water, filter the mixture, separate off the organic phase, dry it and evaporate off the solvent in vacuo. The residue obtained is purified by chromatography over silica gel using a mixture of cyclohexane/ethyl acetate: 90/10 as eluant, followed by crystallisation from the same solvent.

Step F: 3H-benzo[e]indole-6-carbonitrile

To a solution of 2.74 g of sodium in 280 ml of dry ethanol add 10 g (0.0297 mol) of the product synthesised in the previous step and heat the mixture at reflux for one hour. After evaporating off the solvent, the residue is taken up in 200 ml of dichloromethane: and the organic phase is washed with 200 ml of water. After evaporation, the residue is purified by chromatography over silica gel using a mixture of cyclohexane/ethyl acetate: 80/20 as eluant.

Step G: 2,3-Dihydro-1H-benzo[e]indole-6-carbonitrile

The experiment protocol for reducing 3H-benzo[e]indole-6-carbonitrile is the same as that of Preparation 1, Step C.

Preparation 4

7-Methoxy-2,3-dihydro-1H-benzo[e]indole

Step A: 6-Methoxy-3,4-dihydro-1(2H)-naphthalenone oxime

Dissolve 100 g (0.57 mol) of 6-methoxy-1-tetralone in 2.5 liters of a mixture of ethanol/water: 80/20. There are then added, at ambient temperature, 85 g (1.04 mol) of sodium acetate and 43 g (0.62 mol) of hydroxylamine hydrochloride. Heat the suspension at reflux for 4 hours. Dilute the mixture with 5 liters of water and extract with ethyl ether, wash with water, dry over magnesium sulphate and filter. After evaporating off the solvent, 99 g of a beige solid are obtained.

Step B: 2-Amino-6-methoxy-3,4-dihydro-1(2H)-naphthalenone

Dissolve 50 g (0.26 mol) of the product synthesised in the previous step in 185 ml of pyridine and then add, at ambient temperature, 54.9 g (0.29 mol) of para-toluenesulphonyl chloride. After 24 hours, pour onto ice and then filter off the precipitate. Take up the precipitate in dichloromethane and wash with water; dry the organic phase over magnesium sulphate and filter. After evaporating off the solvent, 89 g of a yellow solid (intermediate product 1) are obtained.

Add 7.48 g (0.32 mol) of sodium to a mixture of toluene/ethanol: 720/148 ml. After dissolution, dilute with 940 ml of toluene and rapidly add 117 g (0.34 mol) of intermediate product 1. After 24 hours at ambient temperature, filter off the sodium para-toluenesulphonate, rinse with toluene, and then pour the organic solution into 10% hydrochloric acid solution (1.1 liters). Separate off, extract once with water and then evaporate the aqueous phase. Take up the residue in ethanol and then filter off the precipitate. 46.5 g of a beige solid in the form of the hydrochloride are obtained.

Step C: N-Ethyl-N'-(6-methoxy-1-oxo-1,2,3,4-tetrahydro-2-naphthyl)urea

Pour 4.77 g (0.044 mol) of ethyl chloroformate at 0° C. into 5 g (0.022 mol) of 2-amino-6-methoxy-3,4-dihydro-2H-naphthalen-1-one dissolved in pyridine. After two hours at ambient temperature, concentrate the pyridine, take up in dichloromethane and then wash the organic phase with 0.1N hydrochloric acid solution and then with saturated sodium hydrogen carbonate solution and water; dry over magnesium sulphate, filter, and evaporate off the solvent. 5.48 g of an orange solid are obtained.

Step D: N-Ethyl-N'-(6-methoxy-1,2,3,4-tetrahydro-2-naphthyl)urea

At 60° C. and under atmospheric pressure, hydrogenate 98 g (0.37 mol) of the product previously prepared in Step C and dissolved in 1.5 liters of ethanol, using 10 g of 5% palladium-on-carbon. After the absorption has ceased, filter off the catalyst and concentrate the solvent in vacuo. 88.2 g of an oil are obtained.

Step E: N-Ethyl-N'-(6-methoxy-2-naphthyl)urea

Dissolve 7.42 g (0.0298 mol) of the product synthesised in the previous step in 100 ml of toluene. Add 13.51 g (0.0595 mol) of dichlorodicyanoquinone and heat at reflux for 30 minutes. Filter off the precipitate at ambient temperature, rinse with toluene and then evaporate off the solvent. The residue is purified by chromatography over silica gel using pure dichloromethane as eluant. 4 g of a grey solid are obtained.

Step F: 6-Methoxy-2-naphthylamine

Dissolve 3.5 g of the product synthesised in the previous step in 65 ml of ethanol and then add a solution of potassium hydroxide in 65 ml of water. After refluxing for 4 hours, filter off, at ambient temperature, the precipitate that is formed. Take up the crude product in dichloromethane and wash with water until neutral; dry over magnesium sulphate, filter off the precipitate and then evaporate off the solvent. 2.02 g of an orange solid are obtained.

Step G: 1-Iodo-6-methoxy-2-naphthylamine 28.2 g (0.16 mol) of the product synthesised in the previous step are dissolved in a mixture of dichloromethane/methanol: 1500/620 ml. To the resulting solution add, at ambient temperature, 56.7 g (0.16 mol) of benzyltrimethylammonium dichloroiodate and 21.2 g (0.212 mol) of calcium carbonate. After 30 minutes, filter off the insoluble material, then take up the organic phase with 10% sodium bisulphite solution and extract with ethyl ether. Dry over magnesium sulphate, filter and evaporate. The residue is purified by chromatography over silica gel, using a mixture of cyclohexane/ethyl acetate: 70/30 as eluant.

Step H: Ethyl 1-iodo-6-methoxy-2-naphthylcarbamate

Conversion of 1-iodo-6-methoxy-2-naphthylamine is carried out by applying the method described in Preparation 3, Step D.

Step I: Ethyl 6-methoxy-1-[(trimethylsilyl)ethanol]-2-naphthylcarbamate

Conversion of ethyl 1-iodo-6-methoxy-2-naphthylcarbamate is carried out by applying the method described in Preparation 3, Step E.

Step J: 7-Methoxy-3H-benzo[e]indole

Conversion of the compound of the previous step is carried out by applying the method described in Preparation 3, Step F.

Step K: 7-Methoxy-2,3-dihydro-1H-benzo[e]indole

The experiment protocol for reducing 7-methoxy-3H-benzo[e]indole is the same as that of Preparation 1, Step C.

EXAMPLE 1

N-(3-Pyridyl)-1,2-dihydro-3H-benzo[e]indole-3-carboxamide

Dissolve 1.92 g (0.013 mol) of nicotinoyl azide in 250 ml of toluene and heat at reflux for 30 minutes. Then cool to 15° C. and rapidly add a solution of 2.4 g (0.013 mol) of the product synthesised in Preparation 1. After a few minutes filter off the precipitate formed, form it into a paste with ethyl ether and recrystallise the residue from 130 ml of ethanol. Filter the crystals.

Melting point: 183–186° C.

EXAMPLE 2

N-(3-Pyridyl)-2,3-dihydro-1H-benzo[f]indole-1-carboxamide hydrochloride

The experiment protocol is the same as that of Example 1, starting from the product of Preparation 2.
Melting point: 235–240° C.

EXAMPLE 3

6-Cyano-N-(3-pyridyl)-1,2-dihydro-3H-benzo[e]-indole-3-carboxamide hydrochloride The experiment protocol is the same as that of Example 1, starting from the product of Preparation 3.
Melting point: 265° C. dec.

EXAMPLE 4

7-Methoxy-N-(3-pyridyl)-1,2-dihydro-3H-benzo[e]-indole-3-carboxamide hydrochloride The experiment protocol is the same as that of Example 1, starting from the product of Preparation 4.
Melting point: >270° C. dec.

PHARMACOLOGICAL STUDY

EXAMPLE 5

Measurement of the Extracellular Concentrations of Dopamine and Noradrenaline in the Frontal Cortex of the Conscious Rat Method:

Dialysis. The surgery is performed under pentobarbital-induced anaesthesia (60 mg/kg, i.p.). The rats are placed in a Kopf stereotaxic device and a cannula guide (CMA Microdialysis AB, Stockholm, Sweden) is implanted in the frontal cortex at the coordinates: anteroposterior: +2.2, lateral: ±0.6, ventral deviation: −0.2. The rats are placed in separate cages and recover from the anaesthesia over 5 days. On the day of the dialysis, a Cuprophan CMA/11 probe (length: 4 mm; ext. dia.: 0.24 mm) is introduced into the guide and perfused at 1 μl/min. with a solution of 147.2 mM NaCl, 4 mM KCl and 2.3 mM $CaCl_2$ adjusted to pH 7.3 with a phosphate buffer. Two hours after implantation, samples of dialysate are collected every 20 minutes for 4 hours. Three baseline samples are collected before administration of the drug.

Chromatography. Dopamine (DA) and noradrenaline (NA) are simultaneously measured as follows: 20 μl of dialysate sample are diluted with 20 μl of mobile phase (75 mM $NaH_2PO_4$, 20 μM EDTA, 1 mM sodium decanesulphonate, 17.5% methanol, 0.01% triethylamine, pH: 5.70) and 33 μl are analysed by HPLC using, for separation, an inversephase column (Hypersil C18, 150×4.6 mm; particle size 5 μm) thermostatically controlled at 43° C. and, for quantification, a coulometric detector (ESA5014, Coulochem II, ESA, Chelmsford, USA). The potential of the first electrode is −90 mV (reduction) and that of the second +280 mV (oxidation). The mobile phase flow rate is 2 ml/min. The sensitivity limits for DA and NA are 0.1 and 0.2 pg, respectively.

Results:

The compound of Example 1 (40.0 mg/kg, p.o.) causes a substantial increase in the extracellular concentrations of DA and NA in the dialysates collected from the frontal cortex of conscious rats. The data are expressed as the mean ±S.E.M. The levels of DA and NA are expressed with respect to the mean values before administration of the drug. 30 minutes post administration the effects of the drug are compared (unpaired t test) to those obtained in animals treated with the solvent.

DA: solvent=+3.9±9.8 versus drug=+95.0±12.9, and NA: solvent=+8.7±11.9 versus drug=+118.2±16.7.

EXAMPLE 6

Penile Erection Test Following Administration of Ro 60-0175 (1.25 mg/kg, s.c.) in the Rat Method:

This test allows evaluation of the capacity of pharmacological agents to inhibit penile erections caused by administration of a selective $5-HT_{2c}$ agonist, Ro 60-0175. Inhibition is therefore predictive of antagonist activity with respect to $5-HT_{2c}$ receptors. Male rats of the Wistar strain (Iffa-Credo, L'Arbresle, France) weighing 120–140 g on the day of the experiment are placed separately in plexiglass observation boxes (7.5×18×30 cm) immediately after the compound or the carrier has been administered. Thirty minutes later, Ro 60-0175 (1.25 mg/kg, s.c.) is administered to the animals and the number of erections occurring during the next 30 minutes is counted.

Results:

| Dose of the compound of Example 1 mg/kg p.o. | % inhibition | $ID_{50}$ mg/kg p.o. |
|---|---|---|
| 0.25 | 12 | |
| 0.63 | 16 | |
| 1.00 | 50 | 1.16 |
| 2.5 | 88 | |
| 10.0 | 100 | |

$ID_{50}$ = inhibitory dose$_{50}$.

EXAMPLE 7

Social Interaction Test in the Rat

Method:

This test allows evaluation of the potential anxiolytic activity of the compounds. Male rats of the Sprague-Dawley strain (Charles River, Saint-Aubin-les-Elbeuf, France) weighing 240–260 g on arrival are isolated in individual cages for 5 days in dimly lit animal quarters (3–10 lux). The test is carried out on the final day and consists of placing the animals in pairs, matched by weight (±5 g), in a brightly lit enclosure (300 lux) for 10 minutes. The time spent by the animals in interacting with one another (grooming, chasing, . . . ) is measured. The compound or the carrier is administered to the animals 1 hour before the test, each couple receiving the same treatment. The anxiolytic effect of a compound is reflected by an increased duration of interaction compared to that of animals to whom the carrier has been administered.

Results:

| Dose of the compound of Example 1 mg/kg p.o. | Duration of social interactions (s) mean ± s.e.m. (n) |
|---|---|
| 0 | 183 ± 7 (12) |
| 0.16 | 187 ± 11 (5) |
| 0.63 | 228 ± 11 (5)* |
| 2.5 | 242 ± 15 (5)* |
| 10.0 | 233 ± 10 (5)* | s.e.m.: standard error of the mean
n: number of rats
Comparison with respect to the carrier (Dunnett's test):
*p < 0.05.

EXAMPLE 8

Vogel Conflict Test

Method:

The test is carried out in a transparent plastics cage (32×25×30 cm) located in a soundproofed and ventilated enclosure. The cage has a chrome steel floor. The metal tip of the drink-containing bottle enters the cage at a height of 6 cm above the metal floor. The floor and the tip of the bottle are connected by electric cables to an "Anxiometer" apparatus (Columbus Instruments, Ohio, USA), which records the licks of the animal and controls the administration of electric shocks.

For the 4 days preceding the test, the rats (male Wistar rats weighing 250–270 g) (3 per cage) have access to drink for only one hour per day. On the day before the test, the animals are isolated in cages, on grills, without food or drink, immediately after their final hour of access to drink. The test takes place on the 5th day. On the day of the test, the animal is given by gavage (p.o.) either the solvent (suspension of distilled water+Tween 80) (control) or the compound, 30 minutes before being placed in the test cage. The session begins as soon as the animal has carried out 20 licks and has received a first electric shock (between the metal tip and metal floor), (constant current, 0.5 sec. duration, 0.3 mA intensity). Subsequently, the animal receives an electric shock each time it carries out 20 licks, for a period of 3 minutes. Animals not having performed the first 20 licks of the session by the end of 5 minutes are withdrawn from the test. The results are the numbers of licks performed by the animal during the 3 minutes of the test.

Results:

| Doses of compound of Example 1 mg/kg, p.o. | Punished licks (1 shock/20 licks) Mean ± s.e.m. (n) |
|---|---|
| 0 | 77.1 ± 14.7 (9) |
| 2.5 | 92.2 ± 20.7 (5) |
| 10.0 | 145.2 ± 46.3 (5) |
| 40.0 | 324.4 ± 70.7 (10)* | s.e.m.: standard error of the mean
n: number of rats
Comparison with respect to the carrier (Dunnett's test):
*p < 0.05.

EXAMPLE 9

Pharmaceutical Composition

Formula for the Preparation of 1000 Tablets Each Containing 10 mg of Active Ingredient

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

The invention claimed is:

1. A method for treating an animal or human living body afflicted with depression, migraine, bulimia and anorexia, comprising the step of administering to the living body an amount of a compound selected from those of formula (I)

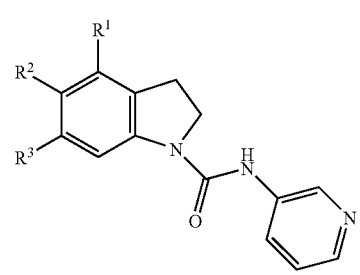

(I)

wherein:
  $R^1$ and $R^2$ together form a benzo ring optionally substituted by halogen or by alkyl, alkoxy, cyano, nitro, hydroxy, amino, alkylamino, dialkylamino or trifluoromethyl, and $R^3$ represents hydrogen,
  or
  $R^1$ represents hydrogen, and $R^2$ and $R^3$ together form a benzo ring optionally substituted by halogen or by alkyl, alkoxy, cyano, nitro, hydroxy, amino, alkylamino, dialkylamino or trifluoromethyl,
  its enantiomers, diastereomers, or addition salts thereof with a pharmaceutically acceptable acid or base,
  it being understood that:

the term "alkyl" denotes a linear or branched (C1–C6) hydrocarbon chain, the term "alkoxy" denotes a linear or branched (C1–C6) alkyl-oxy group, which is effective for alleviation of the conditions.

2. A method of claim 1, wherein $R^1$ and $R^2$ together form a benzo ring which is unsubstituted or substituted by a group selected from methoxy and cyano.

3. A method of claim 1, wherein the compound of formula (I) is selected from N-(3-pyridyl)-1,2-dihydro-3H-benzo[e]indole-3-carboxamide or its addition salts thereof with a pharmaceutically acceptable acid or base.

4. A method of claim 1, wherein the compound of formula (I) is selected from 7-methoxy-N-(3-pyridyl)-1,2-dihydro-3H-benzo[e]indole-3-carboxamide or its addition salts thereof with a pharmaceutically acceptable acid or base.

5. A method of claim 1, wherein the compound of formula (I) is selected from 6-cyano-N-(3-pyridyl)-1,2-dihydro-3H-benzo[e]indole-3-carboxamide or its addition salts thereof with a pharmaceutically acceptable acid or base.

6. A method of claim 1, wherein the compound of formula (I) is selected from N-(3-pyridyl)-2,3-dihydro-1H-benzo[f]indole-1-carboxamide or its addition salts thereof with a pharmaceutically acceptable acid or base.

7. A method for inhibiting penile erection in an animal or human living body, comprising the step of administering to the living body an amount of a compound selected from those of formula (I)

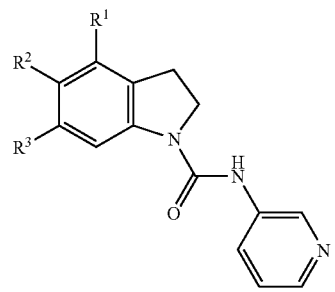

(I)

wherein:
$R^1$ and $R^2$ together form a benzo ring optionally substituted by halogen or by alkyl, alkoxy, cyano, nitro, hydroxy, amino, alkylamino, dialkylamino or trifluoromethyl, and $R^3$ represents hydrogen, or $R^1$ represents hydrogen, and $R^2$ and $R^3$ together form a benzo ring optionally substituted by halogen or by alkyl, alkoxy, cyano, nitro, hydroxy, amino, alkylamino, dialkylamino or trifluoromethyl, its enantiomers, diastereomers, or addition salts thereof with a pharmaceutically acceptable acid or base, it being understood that:

the term "alkyl" denotes a linear or branched (C1–C6) hydrocarbon chain, the term "alkoxy" denotes a linear or branched (C1–C6) alkyl-oxy group, which is effective for inhibition of penile erection.

* * * * *

UNITED STATES PATENT AND TRADEMARK OFFICE
CERTIFICATE OF CORRECTION

PATENT NO. : 7,053,108 B2
APPLICATION NO. : 10/813347
DATED : May 30, 2006
INVENTOR(S) : Gilbert Lavielle et al.

It is certified that error appears in the above-identified patent and that said Letters Patent is hereby corrected as shown below:

Column 11 Line 1:   "(C1-C6)" should be --$(C_1-C_6)$--.

Column 11 Line 3:   "(C1-C6)" should be --$(C_1-C_6)$--.

Column 12 Line 29:  "(C1-C6)" should be --$(C_1-C_6)$--.

Column 12 Line 31:  "(C1-C6)" should be --$(C_1-C_6)$--.

Signed and Sealed this

Twelfth Day of September, 2006

JON W. DUDAS
*Director of the United States Patent and Trademark Office*